(12) United States Patent
Tsuchiyama et al.

(10) Patent No.: US 7,781,210 B2
(45) Date of Patent: Aug. 24, 2010

(54) EPSTEIN-BARR VIRUS-NEGATIVE NK CELL LINE

(75) Inventors: Junjiro Tsuchiyama, 1-77-1, Sekiyahonson-cho, Niigata-shi, Niigata 951-8162 (JP); Tadashi Yoshino, Okayama (JP); Mine Harada, Okayama (JP)

(73) Assignee: Junjiro Tsuchiyama, Niigata (JP)

( * ) Notice: Subject to any disclaimer, the term of this patent is extended or adjusted under 35 U.S.C. 154(b) by 1108 days.

(21) Appl. No.: 10/486,484

(22) PCT Filed: Mar. 22, 2002

(86) PCT No.: PCT/JP02/02765

§ 371 (c)(1), (2), (4) Date: Jul. 30, 2004

(87) PCT Pub. No.: WO03/016513

PCT Pub. Date: Feb. 27, 2003

(65) Prior Publication Data

US 2004/0253579 A1   Dec. 16, 2004

(30) Foreign Application Priority Data

Aug. 13, 2001 (JP) .............................. 2001-245757

(51) Int. Cl.
*C12N 15/85* (2006.01)
*C12N 7/00* (2006.01)
*C12N 1/70* (2006.01)
*C12P 21/00* (2006.01)

(52) U.S. Cl. .................. 435/325; 435/235.1; 435/5; 435/70.1

(58) Field of Classification Search .................. None
See application file for complete search history.

(56) References Cited

OTHER PUBLICATIONS

Hercend et al., Generation of a cloned NK cell line derived from the "null cell" fraction of a human peripheral blood. 1982, The Journal of Immunology, vol. 129, p. 1299-1305.*
Yagita et al. Leukemia, May 2000, vol. 14, p. 922-930.*
Yagita et al. (Leukemia, May 2000, vol. 14. p. 922-930).*
Srivastava et al. (Leukemia Research, 2005, vol. 29, p. 771-783).*
Ho et al. (Molecular and Cellular Biology, 2005, vol. 25, p. 7423-7431).*
Shimizu et al (Journal of Virology, 2004, p. 6069-6073).*
Tsuchiyama et al (Blood, 1998, p. 1374-1383).*
Nakashima et al., "Genome-wide array-based comparative genomic hybridization of natural killer cell lymphoma/leukemia: Different genomic alteration patterns of aggressive NK-cell leukemia and extranodal Nk/T-cell lymphoma, nasal type," Gen. Chr. Can. 44(3):247-255 (2005) (abstract only).
Gebhart, "Genomic imbalances in human leukemia and lymphoma detected by comparative genomic hybridization (Review)," Int. J. Oncol. 27(3):593-606 (2005) (full text).
"Myc/Max/Mad," *Tenshainshi, Bio Science Shin-yogo Library*, $2^{nd}$ Ed., pp. 177-179 (1999) (with English translation).
Sugimoto et al., "Molecular Analysis of Oncogenes, *ras* Family Genes (*N-ras, K-ras, H-ras*), *myc* Family Genes (*c-myc, N-myc*) and *mdm2* in Natural Killer Cell Neoplasms," *Jpn. J. Cancer Res.*, 93:1270-1277 (2002).
Maruo and Takata, "Loss of EBV genome in Burkitt's lymphoma cell line by transfection of EBERs gene," *Annual Meeting of the Japanese Cancer Association*, Abst. No. 207, p. 141 (1999).
Tsuchiyama J. et al., Int. J. Hematol, vol. 73 (Suppl. 1), p. 72(Abstract No. 112) (2001) (with translation).
Tsuchiyama J. et al., $63^{rd}$ Annual Meeting of the Japanese Society of Hematology (Apr. 2001) (with concise summary).
Tsuchiyama J. et al., Blood, vol. 92(4), pp. 1374-1383 (1998).
Shimizu N. et al., J. Virol., vol. 68(9), pp. 6069-6073 (1994).
Zarling M. et al., J. Immunol., vol. 127(5), pp. 2118-2123 (1981).
Drexler H.G. and Matsuo Y., "Malignant hematopoietic cell lines: in vitro models for the study of natural killer cell leukemia-lymphoma," Leukemia, vol. 14(5), pp. 777-782 (2000).
Jaffe ES et al., "Report of the Workshop on Nasal and Related Extranodal Angiocentric T/Natural Killer Cell Lymphomas", The American Journal of Surgical Pathology, vol. 20(1), pp. 103-111 (1996).
Uno M. et al., "In Vitro Induction of apoptosis for nasal angiocentric natural killer cell lymphoma-derived cell line, NK-YS, by etoposide and cyclosporine A," British Journal of Haematology, vol. 113, pp. 1009-1014 (2001).
Nuguchi T. et al., "Antisense oligodeoxynucleotides to latent membrane protein 1 induce growth inhibition, apoptosis and Bcl-2 suppression in Epstein-Barr virus (EBV)-transformed B-lymphoblastoid cells but not in EBV-positive natural killer cell lymphoma cells," British Journal of Haematology, vol. 114, pp. 84-92 (2001).

* cited by examiner

*Primary Examiner*—Zachariah Lucas
*Assistant Examiner*—Agnieszka Boesen
(74) *Attorney, Agent, or Firm*—Fish & Richardson P.C.

(57) ABSTRACT

The present invention provides Epstein-Barr virus (EBV)-negative NK cell lines. The NK cell lines of the present invention are useful for screening factors associated with the proliferation and expression functions of NK cells and to discover factors produced by the NK cells. In addition, the cell lines are immortalized despite the fact that they are EBV-negative. Thus, unknown mechanisms of oncogenesis may be elucidated through an understanding of the mechanisms underlying the immortalization of the cell lines of the present invention.

24 Claims, 10 Drawing Sheets

NK-TY2 (EBV-)

NK-YS (EBV+)

50, X,-X,+2, add(3)(p21), der(4)t(4;9)(q35;q12),del(6)(q13),
+del(6), +i(7)(q10), add(9)(p22),del(11)(q13q21),
der(14;16)(q10;p10), der(17)dup(17)(q21q25)t(1;17)(q12;q25),
+19, +21, +mar L, LAD CELL; YS, NK-YS; TY2, NK-TY2; J, Jurkat

EPSTEIN-BARR VIRUS-NEGATIVE NK CELL LINE

TECHNICAL FIELD

The present invention relates to an NK cell line.

BACKGROUND ART

A natural killer cell (hereinafter abbreviated as "NK cell") is activated by interferon and interleukin-2 (hereinafter abbreviated as "IL2"), and the activated cell destroys tumor cells and such. While the biological defense mechanism dependent on T cells and B cells functions as a result of immune response, the NK cell-dependent defense mechanism works via the activation by cytokines. Namely, the complicated process of immune response is not required for the defensive function of NK cells. Therefore, NK cells have been believed to play an important role at the forefront of the biological defense mechanisms.

Thus, the biological defense mechanisms may be controlled by modifying the activation and proliferation of NK cells. However, many obscurities regarding the function of NK cells remain to be clarified.

On the other hand, NK cells are lymphocytes and form lymphomas upon tumorigenic transformation. For example, primary nasal angiocentric NK lymphoma is a lymphoma found in Asian countries. Primary nasal angiocentric NK lymphomas are generally resistant to various anti-cancer agents and often have a bad prognosis. Thus, elucidation of the mechanism of NK cell tumorigenesis is an important object for developing therapeutic methods against this disease.

Infection with Epstein-Barr virus (hereinafter abbreviated as "EBV") has been suggested to be involved in the development lymphoma. For example, using a cell line established from Burkitt's lymphoma (hereinafter abbreviated as "BL"), the influence of the EBV genome on B cell lymphoma has been reported (Journal of Virology 6069-6073, 1994, "Isolation of Epstein-Barr Virus (EBV)-negative cell clones from the EBV-positive Burkitt's lymphoma (BL) line Akata: malignant phenotypes of BL cell are dependent on EBV."). According to this report, malignant phenotypes of BL were induced in EBV-negative Akata cells by infection of EBV into the cells. However, there is no report describing the involvement of EBV with NK cells. Thus, elucidation of the mechanism underlying the tumorigenesis of NK cells is desired in the art. In particular, once an EBV-negative NK cell line is established, such a cell line can serve as an important research tool for studying the effect of EBV on NK cells.

NK cell lines are useful for performing studies on NK cells, e.g., studies on the regulation of activation and proliferation of NK cells, the mechanism underlying NK cell tumorigenesis, etc. When such a cell line is made available, a common cell can be easily shared by many researchers. Most importantly, the use of a cell line obviates the need to use fresh blood as an experimental tool, which would facilitate the performance of such experiments.

The present inventors have already established a cell line NK-YS derived from NK lymphoma (Blood 192: 1374-1383, 1998). The NK cell line NK-YS is an EBV-positive cell line. To assess the involvement of EBV, it is expected to establish an EBV-negative cell line.

As described above, the establishment of an EBV-negative cell line from an Akata cell that is a B-cell lymphoma-derived cell line has been reported. The elimination of EBV in B cells occurs due to long-term passage of EBV-positive lymphoma-derived cells. This enabled the establishment of an EBV-negative B cell line. However, there is no known technique to establish EBV-negative NK cell lines.

DISCLOSURE OF THE INVENTION

An objective of the present invention is to provide EBV-negative NK cell lines and uses thereof.

To achieve the above-described objective, the present inventors repeatedly separated various NK cells and examined whether the cells were infected with EBV. As a result, the present inventors successfully established an EBV-negative cell line from NK cells derived from a patient with primary nasal lymphoma. The present inventors also discovered that activities to control the NK cell activity can be detected using this NK cell line; and thus, the present invention was completed. Specifically, the present invention provides cell lines, methods for detecting activities to control the NK cell activity using the cell lines, and screening method using the cell lines as follows.

[1] An Epstein-Barr virus-negative NK cell line.

[2] The cell line according to [1], which is derived from human.

[3] The cell line according to [1], which is derived from a leukemia cell.

[4] The cell line according to [3], wherein the leukemia is a lymphoma.

[5] The cell line according to [4], wherein the lymphoma is a nasal angiocentric lymphoma.

[6] The cell line according to [5], wherein the nasal angiocentric lymphoma is an NK lymphoma.

[7] The cell line according to [1], which is derived from an Epstein-Barr virus-positive host.

[8] The cell line according to [1], which is positive in CD2, CD16, CD33, CD38, and CD56.

[9] The cell line according to [1], which is negative in CD3, CD4, CD8, CD19, CD20, and CD34.

[10] The human NK cell line NK-TY2 deposited under the accession number FERM BP-7865.

[11] An Epstein-Barr virus-infected cell of the cell line according to [1].

[12] A method for detecting an ability to control NK cell activity, which comprises the steps of:

(1) contacting a test compound with the cell line according to [1] or a cell derived from the cell line; and (2) determining an activity of said cell and comparing the activity with that of a control.

[13] The method according to [12], wherein the cell line is the human NK cell line NK-TY2 deposited under the accession number FERM BP-7865.

[14] A method of screening for a compound having the ability to control NK cell activity, which comprises the steps of:

(1) detecting an ability of a test compound to control NK cell activity according to the method of [12]; and (2) selecting a compound that enhances or suppresses NK cell activity by comparing the activity with that of a control.

[15] A kit for screening compounds that have an ability to control the NK cell activity, which comprises:

(a) the cell line according to [1]; and (b) a reagent for assaying an NK cell activity.

[16] A pharmaceutical agent for controlling the NK cell activity, which comprises the compound selected by the screening method according to [14] as an active ingredient.

The present invention also relates to a method for controlling NK cell activity, which comprises the step of administering the compound selected by the screening method according to [14]. Furthermore, the present invention relates to a method for treating NK lymphomas, which comprises the step of administering the compound selected by the screening method according to [14].

The NK cell lines of the present invention are characteristically EBV-negative. Such cell lines can be obtained, for example, through long-term passage of leukemia cells. There is no limitation on the leukemia cells so long as they are NK cells. Furthermore, the NK cells may be derived from any source. Preferably, cells derived from a human lymphoma patient are used. Among others, mononuclear cells isolated from peripheral blood of primary nasal lymphoma patients are preferred leukemia cells. A high rate of EBV infection has been reported in primary nasal lymphomas. Thus, it is quite meaningful to clarify the correlation between lymphoma and EBV using an EBV-negative cell line established from a primary nasal lymphoma patient. Iscove's modified Dulbecco's medium (IMDM) culture medium (supplemented with 10% fetal bovine serum and 100 units of recombinant human IL2 (hereinafter abbreviated as "rhIL2"; Shionogi & Co. Ltd., Osaka, Japan)) or such may be used to culture the mononuclear cells. The cells should be maintained under humid atmosphere with 5% $CO_2$ at 37° C.

In the present invention, there is no limitation on the conditions of the long-term passage. The presence of EBV may be confirmed, for example, by cloning after four months, typically after six months, preferably after seven or eight months of passage. The cloning of cells can be performed according to known techniques, such as the limiting dilution method.

Takata et al. have reported that the introduction of EBV-encoded small RNA 1 (EBER-1) gene eliminates EBV from Burkitt's lymphoma (in the annual meeting of The Japanese Cancer Association in 1999). The elimination of EBV from cells derived from primary nasal lymphoma may be accomplished by the application of this method.

In general, cells, excluding T cells, having killer cell activity (NK activity) are referred to as "NK cells". However, some tumor cells lack the killer cell activity (NK activity). Such cells lacking NK activity can be confirmed as NK cells based on the presence of NK cell characteristic cell surface markers or cytotoxic molecules. An exemplary expression pattern of cell surface markers that indicates a cell to be an NK cell is shown below. These markers can be immunologically detected by known methods using commercially available antibodies.

| | |
|---|---|
| T cell receptor (TcR) | negative |
| CD3 | negative |
| CD56 | positive |
| NK receptor | positive |

NK receptors include marker molecules such as CD94, CD158a, CD158b, CD158c, CD159, CD161, and NKG2A. When a cell is positive for at least one of these marker molecules, it is judged to be NK receptor positive. Typically, plural markers are used as indicators.

Known cytotoxic molecules include perforin, TIA-1, Fas, Fas-L, IFN-γ, IFN-α, and Granzyme B. Likewise, a cell detected to have at least one of the cytotoxic molecules is judged to be cytotoxic molecule positive. Antibodies recognizing these cytotoxic molecules are commercially available. Therefore, they can be detected according to known methods, such as via the immunofluorescent antibody method.

As used herein, the term "NK cells" refers to cells either belonging to group A or group B described below.

| Group A: | | Group B: | |
|---|---|---|---|
| With killer cell activity (NK activity) | | T cell receptor (TcR) | negative |
| CD3 | negative | CD3 | negative |
| CD56 | positive | CD56 | positive |
| T cell receptor (TcR) | negative | NK receptor | positive |
| TcR gene rearrangement | negative | Cytotoxic molecule | positive |

The presence of EBV in a cloned cell line can be confirmed, for example, by detecting the EBV genome. More specifically, for example, Southern blotting may be carried out using, as a sample, DNAs obtained by digesting the genome of the cell line with an appropriate restriction enzyme. Alternatively, EBV may be effectively detected by in-situ hybridization using the EBV genome as the target. Furthermore, PCR methods may be used to detect the EBV genome. The terminal repeat of EBV, for example, may be used as a probe for Southern blotting. An EBER-1 antisense oligonucleotide can be used as a probe in the in-situ hybridization. Protocols for the Southern blotting and in-situ hybridization are well known in the art.

EBV infection can be also confirmed using a technique wherein a cell surface EBV antigen (Epstein-Barr nuclear antigen; EBNA) is detected. The detection of EBNA suggests the presence of EBV. Thus, such a technique is an advantageous assay procedure, as a screening method to eliminate EBV-positive cells.

The NK cell lines of the present invention include the human NK cell line, NK-TY2, deposited under the accession number FERM BP-7865, internationally under the Budapest Treaty.

Depository Information:

(a) Name and Address of Depositary Institution

Name: International Patent Organism Depositary, National Institute of Advanced Industrial Science and Technology (AIST) (Previous Name: The National Institute of Bioscience and Human-Technology, The Agency of Industrial Science and Technology, The Ministry of International Trade and Industry)

Address: AIST Tsukuba Central 6, 1-1-1 Higashi, Tsukuba, Ibaraki, Japan (ZIP CODE: 305-8566)

(b) Date of Deposition (Date of initial deposition): May 22, 2001

(c) Accession Number: 7865 (FERM BP-7865)

NK-TY2 is an EBV-negative NK cell line established by the present inventors through the long-term passage of mononuclear cells isolated from the peripheral blood of a primary nasal angiocentric lymphoma from an EBV positive patient. The immunological phenotype of NK-TY2 is shown below. The NK-TY2 cell retains the phenotype of the original leukemia cell.

| | |
|---|---|
| CD2, CD16, CD33, CD38, and CD56 | positive |
| CD3, CD4, CD8, CD19, CD20, and CD34 | negative |

According to analyses described herein, NK-TY2 was discovered to be a cell line having the features shown below. Judging from these features, it is clear that NK-TY2 is an NK cell.

| | | | |
|---|---|---|---|
| T cell receptor (TcR) | negative | CD56 | positive |
| TcR gene rearrangement | negative | NK receptor | positive (CD94 and NKG2A positive) |
| CD3 | negative | Cytotoxic molecule | Positive (perforin positive) |

There are no limitations on the conditions for culturing the cell lines of the present invention. Thus, the cells can be cultured under arbitrary conditions which do not exterminate the cells but allow them to survive or proliferate. For example, a typical culture temperature ranges from 33° C. to 39° C., and is preferably 37° C. An IMDM medium containing 3% to 10% (preferably 10%) fetal bovine serum, preferably inactivated fetal bovine serum (i.e., fetal bovine serum heat-treated to inactivate the complements) is used as the culture medium. The culture is maintained under an atmosphere of 5% $CO_2$ with 80%-120% (preferably 100%) humidity.

Furthermore, there are no limitations on the conditions for storing the cell lines of the present invention. The cells can be cryopreserved, for example, at −80° C. or in liquid nitrogen, presuspended at a cell density of $10^2$-$10^{10}$ cells/ml, preferably $10^4$-$10^8$ cells/ml, and more preferably $10^6$ cells/ml in a culture medium containing 10% glycerin, or 10% dimethyl sulfoxide and 10% serum. Preferably, the cells are cryopreserved in liquid nitrogen, suspended at a cell density of $10^6$ cells/ml in a culture medium containing 10% glycerin and 10% serum. The cell line stored as described above can be grown again, for example, by rapidly thawing the cells in a water bath at 37° C.; adding 10 volumes of medium containing 10% serum; stirring; collecting cells by centrifugation; and then culturing the cells in medium containing 10% serum.

The NK cell lines of the present invention are useful as a research tool to elucidate the mechanism of oncogenesis. Although the EBV genome is eliminated, the NK cell lines of the present invention remain in an immortalized state. This suggests that these cell lines have acquired some mutations accommodate for the function of the EBV genome. Thus, the oncogenic mechanism of lymphoma may be elucidated through analyses of the NK cell lines of the present invention. More specifically, cancerous mutations in lymphomas can be identified, for example, through analyses of alterations in the expression levels or mutations of known cancer-associated genes, such as p53, p15, p16, p21, RB, bcl-2, and bcl-X, using the cells of the present invention.

For example, as revealed in the Examples, enhanced expression of c-myc and p53 was observed in NK-TY-2, an NK cell line of the present invention. In addition, NK-TY2 was found to be less dependent on IL2 and fetal bovine serum as compared to an EBV-positive cell line, NK-YS. This indicates that the cell line of the present invention, NK-TY2, may have acquired a more malignant character, even though it is negative in EBV. Such changes at the cellular level may be important factors involved in cancerous changes of lymphomas. In other words, the EBV-negative NK cell lines of the present invention are useful research tools in elucidating the canceration mechanism of lymphomas.

As described above, EBV is suspected to play a role in lymphomas. However, particularly in Japan, while the incidence of inapparent EBV infection is observed among many adults, only some of them develop leukemia. Therefore, EBV infection alone is not responsible for the pathology of leukemia. Since the NK cell lines of the present invention are EBV-negative, experiments can be carried out without the influence of EBV.

Alternatively, the process of lymphoma metastasis can be studied by analyzing endothelial damage caused by the NK cell lines of the present invention. More specifically, factors involved in the endothelial damage caused by NK cells can be identified by detecting the activity of anti-NK receptor antibodies and various adhesion molecules that inhibit endothelial damage.

In addition, NK cell lines of the present invention derived from lymphoma patients are useful in methods for assessing or of screening for compounds that are effective for treating lymphoma. Cell lines established from patients with poor prognosis, such as primary nasal lymphoma patients, are particularly useful, because they allow the screening for therapeutic agents against diseases that are difficult to treat. Specifically, when the NK cell lines of the present invention have drug resistance, the drug resistance mechanism of NK lymphoma can be elucidated using the inventive cell lines as a research tool. Chemical therapy is an important therapeutic method for the treatment of lymphomas. Thus, the elucidation of the drug resistance mechanism of lymphoma is an important area of study.

In addition, since the NK cell lines of the present invention are EBV negative, they can be used for the isolation and expansion of EBV. The presence of EBV in a clinical specimen can be detected, for example, by inoculating the clinical specimen, such as blood, with the NK cell lines of the present invention and confirming the infection of EBV. EBV infection in adults who have never been infected can cause infectious mononucleosis. Thus, the detection of EBV in clinical specimens is useful for diagnosing infectious mononucleosis. The infection of EBV into cells allows their detection after the proliferation of the virus. Thus, highly sensitive measurements can be achieved by the EBV-detecting method using the NK cells of the present invention. Furthermore, the presence of infectious EBV virus can be confirmed by performing infection experiments.

Furthermore, EBV can be infected to the NK cell lines of the present invention. The changes in cellular character due to EBV infection can be analyzed using an EBV-infected NK cell line. Such analysis can provide important information for identifying the role of EBV in NK tumor. For example, the involvement of EBV in the malignancy of NK tumor cells can be studied using the cell lines of the present invention. The changes in the character of the cell lines of the present invention may be detected by comparing the colony formation ability in soft agar, tumor formation ability in nude mice, or the sensitivity to serum concentration in the culture medium. The EBV infection to the NK cell lines of the present invention can be achieved by inoculating EBV with a culture of the inventive cell lines. EBV can be obtained from lysate of EBV-infected cell lines, culture supernatant of EBV-producing cells, and such.

Furthermore, the functions of respective genes of EBV can be determined by constructing various EBV mutants, having deletions and mutations introduced into the genes, and studying changes in infectivity to the cells of the present invention or characteristic changes of the cells after infection.

Moreover, tumor cells resistant to the NK cells can be obtained using the NK cell lines of the present invention. A tumor cell resistant to the NK cells can be obtained, for example, by selecting tumor cells that can grow in a co-culture with the NK cells of the present invention. The mechanism of an NK cell-resistant tumor cell to evade damage by the NK cells can be examined by comparing the obtained tumor cell with an NK cell-sensitive tumor cell.

In addition, the NK cell lines of the present invention are useful as a research tool to discover novel physiologically active substances produced by the NK cells. Such physiologically active substances include antiviral substances and antimicrobial substances. Since the NK cell lines of the present invention are EBV negative, physiologically active substances specific to NK cells can be exclusively identified without contamination of physiologically active substances whose production is induced by EBV-derived substances.

The NK cell lines of the present invention are further useful for detecting an ability to control NK cell activity. As used herein, the phrase "NK cell activity" refers to physiological functions of the NK cells. More specifically, "NK cell activity" comprises cell growth activity, the activity of NK cells to produce various factors, and so on. Cytokines regulating the NK cells can be identified, for example, by examining responses of the NK cell lines of the present invention to various cytokines. In addition, the cell lines of the present invention can be used as research tools to elucidate the signal transduction system mediated by the NK receptor or its functions.

For example, NK cells are known to proliferate in an IL2-dependent manner. However, though CD25 and CD122 are predicted to be required for IL2-mediated signaling, they are not detectable in typical NK cells. Thus, the NK cell lines of the present invention can also be used to elucidate the IL2 response mechanism of NK cells because they proliferate in an IL2-dependent manner.

The method of the present invention for detecting an ability to control NK cell activity comprises the steps of:

(1) contacting a test compound with an NK cell line of the present invention or a cell derived from the NK cell line; and (2) determining an activity of said cell and comparing the activity with that of a control.

The above-described cell derived from the NK cell lines of the present invention includes mutant cell lines derived therefrom and transformants thereof transformed with a certain gene.

According to the method for detecting an ability to control NK cell activity of the present invention, the NK cell activity may be determined by measuring the activity of interest. Specifically, for example, when the activity is one that influences the proliferation activity of the cell, then the detection methods of the present invention may be performed by observing cell proliferation. The proliferation of NK cells can be measured by monitoring $[^3H]$-thymidine uptake.

On the other hand, various factors, such as cytokines, may be measured to study influences on the activities of an NK cell to produce the respective factors. Alternatively, mRNAs of the respective factors may be assayed by RT-PCR or such. Controls to be used in the present invention include the NK cells of the present invention that are not contacted with the test compound, and those contacted with compounds with known effects.

The screening of compounds that control NK cell activity can be achieved by selecting compounds for which the ability to control NK cell activity was detected by the above-described detection method of the present invention. Specifically, the present invention relates to a method of screening for a compound that has the activity to control NK cell activity, which comprises the steps of:

(1) contacting a test compound with an NK cell line of the present invention or a cell derived from the NK cell line;

(2) determining an activity of said cell, and comparing the activity with that of a control; and (3) selecting a compound that enhances or suppresses the NK cell activity as compared to that of the control.

For example, compounds that suppress the proliferation or malignant transformation of the NK cells of the present invention act not on EBV but directly on NK cells. Conversely, when using EBV-positive cells, it is difficult to determine whether a particular compound is acting on the cells themselves or on the EBV infected to the cells. Thus, the screening method using NK cells of the present invention is useful for selecting compounds that directly act on the NK cells.

There is no limitation on the test compounds used in the screening method of the present invention. For example, cell extracts, cell culture supernatants, fermentation products of microorganisms, extracts of marine organisms, plant extracts, purified or rough-purified polypeptides, non-peptidic compounds, synthetic low-molecular-weight compounds, and natural compounds, can be screened according to the screening method of the present invention.

NK cells play an important role in the biological defense mechanism. Thus, a compound having the activity to control NK cell activity can be used to control immunological functions. The phrase "control NK cell activity" includes enhancement and suppression of NK cell activity. For example, a compound having the activity to enhance NK cell activity is expected to potentiate immunological functions.

Conversely, a compound that suppresses an activity of the NK cell lines of the present invention is anticipated to serve as a therapeutic agent for NK lymphoma. In particular, when a compound that suppresses the proliferation of a cell line is established from a patient with poor prognosis, such as primary nasal lymphoma patient, it may be useful as a novel therapeutic agent for lymphoma. For example, therapeutic effects of anti-CD56 antibody, anti-CD25 antibody, or such on NK tumors can be assessed. The therapeutic effects can be evaluated using cell death as an indicator.

Compounds that can be isolated by the screening method of the present invention described above can be used to control NK cell activity. Such compounds include compounds that enhance as well as compounds that suppress NK cell activity. NK cells are believed to play an important role in the biological defense mechanism. Thus, the screening method of the present invention can be used to assess or isolate compounds that control the NK cell-mediated biological defense mechanism.

A kit for screening compounds that have the ability to control NK cell activity can be constructed by combining an NK cell line required for the screening method of the present invention and a reagent necessary for the detection of the NK cell activity. In the present invention, the reagent for detecting the NK cell activity can be appropriately selected depending on the type of activity to be used as an indicator. For example, when cell proliferation is to be monitored, $^3H$-labeled thymidine or such may be used as the reagent. Alternatively, the level of a factor produced by the NK cell can be measured using an antibody against the factor as an indicator. Furthermore, primers or probes for detecting mRNA of the factor can be used as the reagent.

A screening kit of the present invention may further contain a culture medium for the NK cell line of the present invention (or a cell derived from the cell lines); additives, such as antibiotics and fetal bovine serum; containers for culture; and so on.

When administering an NK cell activity controlling compound obtained by the method of the invention as a pharmaceutical for humans, other mammals, and so on, such as mice, rats, guinea-pigs, rabbits, chicken, cats, dogs, sheep, pigs, cattle, monkeys, baboons, and chimpanzees, the compound can be directly administered or can be formulated into a dosage form using known pharmaceutical preparation methods. For example, as needed, the compound can be taken orally, as sugar-coated tablets, capsules, elixirs, and microcapsules, or non-orally, in the form of injections of sterile solutions or suspensions with water or any other pharmaceutically acceptable liquid. For example, the compound can be mixed with pharmacologically acceptable carriers or media, specifically, sterilized water, physiological saline, plant-oil, emulsifiers, suspending agents, surfactants, stabilizers, flavoring agents, excipients, vehicles, preservatives, binders, and such, in a unit dose form required for generally accepted drug implementation. The amount of active ingredient in the preparations makes a suitable dosage within the indicated range acquirable.

Examples of additives that can be mixed to tablets and capsules include binders such as gelatin, corn starch, tragacanth gum, and arabic gum; excipients such as crystalline cellulose; swelling agents such as corn starch, gelatin, and alginic acid; lubricants such as magnesium stearate; sweeteners such as sucrose, lactose, and saccharin; flavoring agents such as peppermint, Gaultheria adenothrix oil, and cherry. When the unit dosage form is a capsule, a liquid carrier, such as oil, can also be included in the above-described ingredients. Sterile composites for injections can be formulated according to normal drug implementations using vehicles such as distilled water used for injections.

Physiological saline, and isotonic liquids containing glucose and/or other adjuvants such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, and non-ionic surfactants, such as Polysorbate 80™ and HCO-50.

Sesame oil or soy-bean oil can be used as an oleaginous liquid and may be used in conjunction with benzyl benzoate or benzyl alcohol as solubilizers and may be formulated with buffer, such as phosphate buffer and sodium acetate buffer; a pain-killer, such as procaine hydrochloride; a stabilizer, such as benzyl alcohol and phenol; and an anti-oxidant. The prepared injection solution may be filled into a suitable ampule.

Methods well known to one skilled in the art may be used to administer the inventive pharmaceutical compound to patients, for example, as intraarterial, intravenous, or subcutaneous injections and also as intranasal, transbronchial, intramuscular, subcutaneous, or oral administrations. The dosage varies according to the body-weight and age of the patient and the administration method selected; however, one skilled in the art can readily determine an appropriate dosage. If the compound is encodable by a DNA, the DNA can be inserted into a vector for gene therapy to perform the therapy. The dosage of the DNA and method of administration vary according to the body-weight, age, and symptoms of the patient, though one skilled in the art can select them suitably.

Although there are some differences according to the patient, target organ, symptom, and administration method, the dose of the compound is about 0.1 mg to 100 mg per day, preferably about 1.0 mg to 50 mg per day, and more preferably about 1.0 mg to 20 mg per day, when administered orally to a normal adult (weight 60 kg).

When administered parenterally, in the form of an injection, to a normal adult (weight 60 kg), although there are some differences according to the patient, target organ, symptom, and administering method, the compound is conveniently intravenously injected at a dose of about 0.01 mg to 30 mg per day, preferably about 0.1 to 20 mg per day, and more preferably about 0.1 to 10 mg per day. Also, in the case of other animals, it is possible to administer an amount converted to 60 kg of body-weight.

All publications describing prior art cited herein are incorporated by reference herein in their entireties.

BEST MODE FOR CARRYING OUT THE INVENTION

The present invention is illustrated in detail below with reference to Examples, but is not to be construed as being limited thereto.

Example 1

Establishment of Cell Line NK-TY2

Mononuclear cells were isolated by the Ficoll-Hypaque method from peripheral blood of a consenting patient after the crisis of leukemia. The patient was a 45 year-old female diagnosed as having primary nasal angiocentric NK lymphoma. The peripheral blood of the patient comprised CD2+, CD3−, CD7+, and CD56+ heteromorphic lymphocytes and the patient was EBV positive.

The isolated mononuclear cells were suspended in Iscove's modified Dulbecco's medium (IMDM; GIBCO, Grand Island, N.Y.) supplemented with 10% fetal bovine serum (FBS; Sanko Junyaku Co., Tokyo, Japan). More than 90% of the cells of this cell preparation were CD56-positive. The mononuclear cells ($1 \times 10^6$ cells) were inoculated into 5 mL of IMDM supplemented with 10% FBS containing 100 units of rhIL2 (Shionogi and Co., Osaka, Japan) in a 25 cm²-culture flask (Falcon 3013; Becton Dickinson, Oxnard, Calif.). This flask was maintained under a humidified atmosphere with 5% $CO_2$ at 37° C. Half of the medium was collected twice a week, centrifuged at 1,000 rpm for 3 min in a plastic tube, and then the pellet was resuspended in 2.5 mL of fresh medium. The suspension was returned to the initial culture flask.

Figure 1:
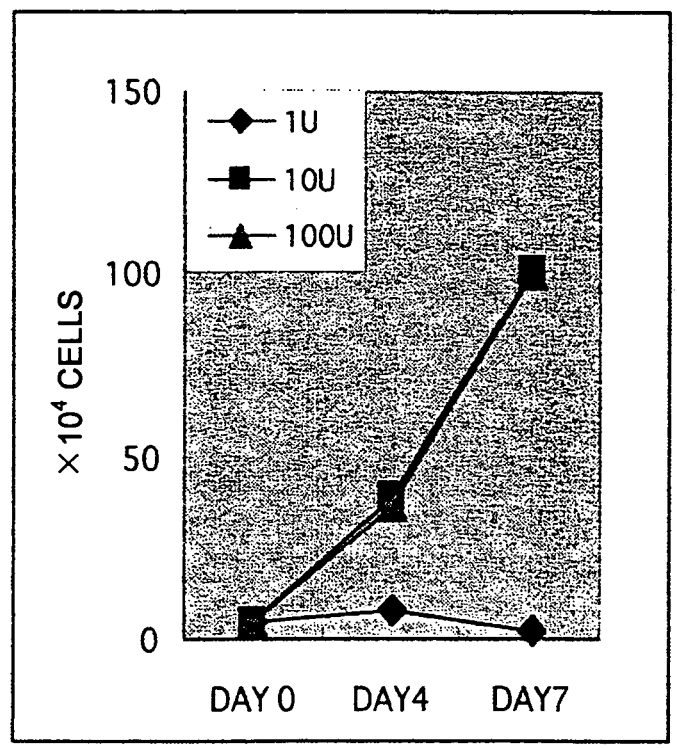
FIG. 1 depicts diagrams showing the IL2 dependency of NK-TY2 cells. In these diagrams, the added amounts of IL2 are as follows: -♦-, 1 U/ml; -■-, 10 U/ml; and -▲-, 100 U/ml. The ordinate indicates the number of cells ($\times 10^4$); the abscissa indicates the days of culture (day).
Figure 1:
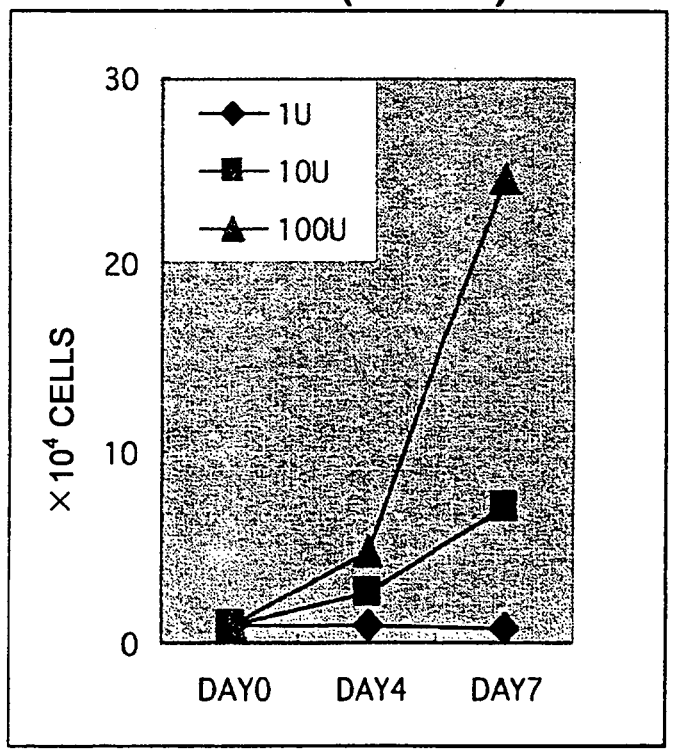
Figure 2:
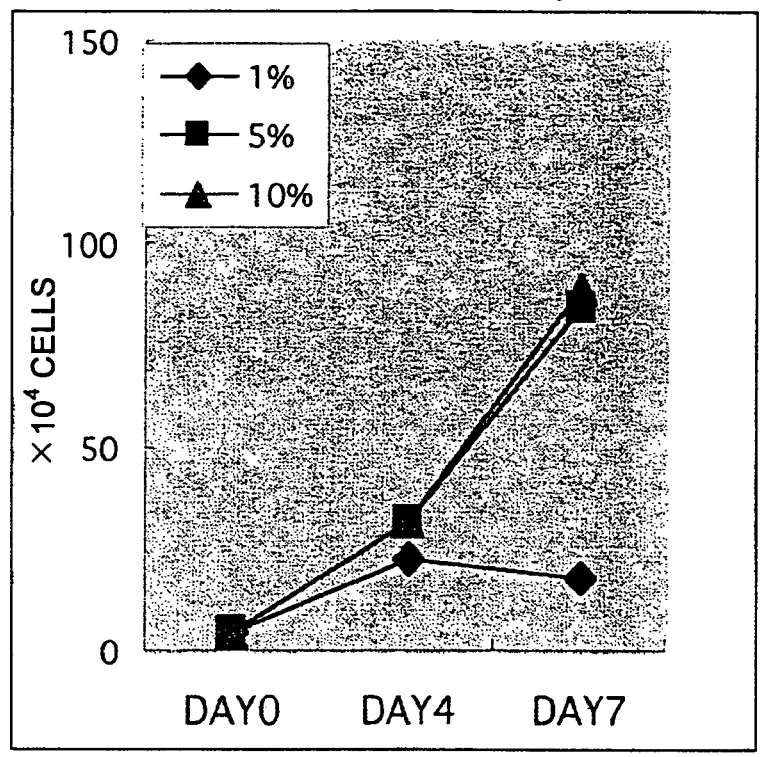
FIG. 2 depicts diagrams showing the fetal bovine serum (FBS) dependency of NK-TY2 cells. In these diagrams, the added amounts of FBS areas follows: -♦-, 1%; -■-, 5%; and -▲-, 10%. The ordinate indicates the number of cells ($\times 10^4$); the abscissa indicates the days of culture (day).
Figure 2:
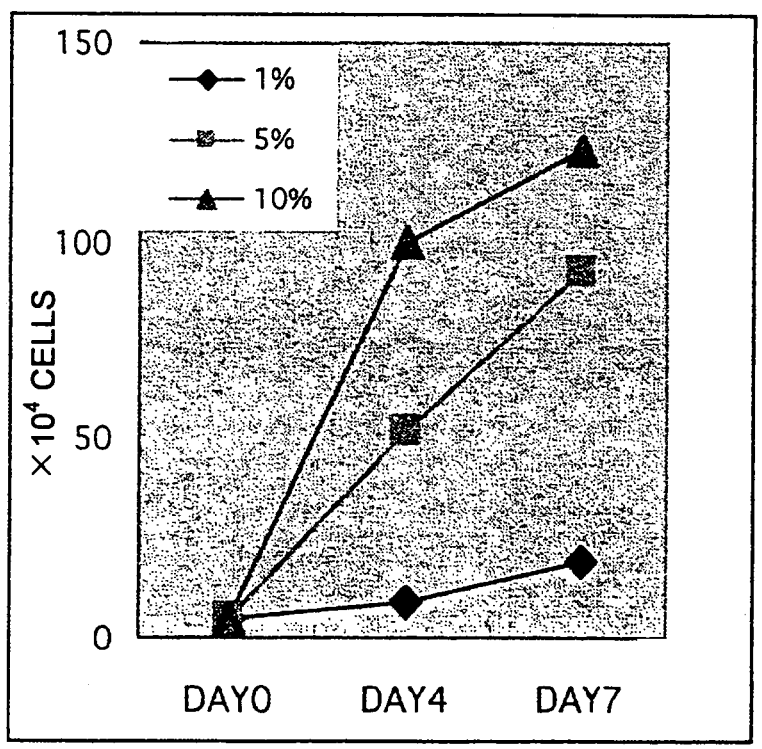

In the primary culture, the leukemic cells proliferated slowly during the first 7 months. Thereafter, the proliferation rate accelerated, and the total number of leukemic cells reached a level of more than $1 \times 10^8$ cells at 8 month of the primary culture. At that time point, the leukemic cells showed stable proliferation. Some of these cells were cryopreserved for subsequent studies. The present inventors then performed cloning by the limited dilution method to establish cell line NK-TY2. The cell doubling time of this cell line was approximately 72 hr (data not shown). The growth of NK-TY2 was IL2-dependent and was enhanced in the presence of IL2 at a concentration of 10 U/ml or more (FIG. 1). The growth of NK-TY2 also depended on FBS and was enhanced in the presence of 5% or more FBS (FIG. 2). NK-TY2 showed smaller dependence on IL2 and FBS as compared to NK-YS, a known NK cell line (EBV+).

Example 2

Morphological Evaluation

Cytocentrifuge smears of the peripheral blood mononuclear cells and NK-TY2 cells were stained with May-Grünwald-Giemsa for observation under a light microscope.

Figure 3:
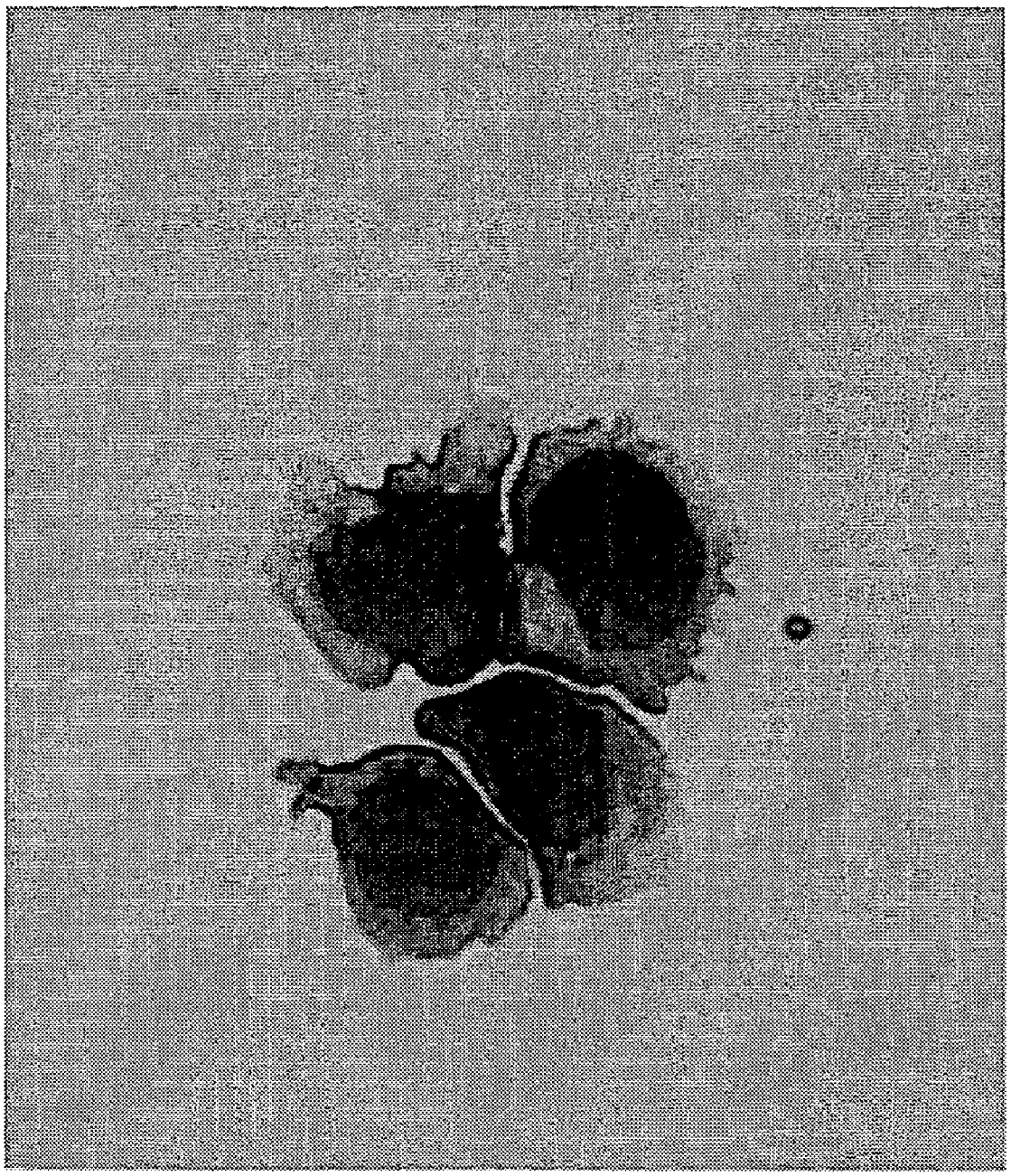
FIG. 3 depicts a photograph of light microscopy showing NK-TY2 cells stained by the May-Grünwald-Giemsa staining method (400-fold).

The result of evaluation showed that NK-YS cells had no azurophilic granules. The cells had large nuclei with coarse chromatin and conspicuous nucleoli, and abundant basophilic cytoplasm (FIG. 3). NK-TY2 cells were negative for peroxidase staining (data not shown).

Example 3

Flow Cytometric Analysis <1> (Cell Marker)

NK-TY2 cells were analyzed by single-color immunofluorescence with a flow cytometer (FACScan; Becton Dickinson and Co., Mountain View, Calif.) for the expression of surface markers. Fluorescein isothiocyanate (FITC)- or phycoerythrin (PE)-conjugated antibodies used in the experiment are shown below:

Leu5b (CD2), Leu4 (CD3), Leu3a (CD4), Leu1 (CD5), Leu9 (CD7), Leu2a (CD8), CALLA (CD10), LFA1α (CD11a), Leu15 (CD11b), LeuM5 (CD11c), LeuM7 (CD13), LeuM3 (CD14), LeuM1 (CD15), Leu11 (CD16), Leu12 (CD19), Leu16 (CD20), CR2 (CD21), IL2R (CD25), LeuM9 (CD33), HPCA1 (CD34), HLe1 (CD45), Leu19 (CD56), Leu7 (CD57), TCR α/β, and SmIg (κ+λ) from Becton-Dickinson;

OKT6 (CD1) from Ortho Diagnostic Systems (Raritan, N.J.);

B1 (CD21) from Coulter Immunology (Hialeah, Fla.);

LFA3 (CD58), Fas (CD95), HP-3B1 (kp43; CD94), EB6 (CD158a), GL183 (CD158b), FES172 (CD158c), Z27.3.7 (CD159), 191B8 (NKRP1A; CD161), and Z199 (NKG2A) from Immunotech (Marseilles, France); and TCR γ/δ from T Cell Sciences (Cambridge, Mass.).

Throughout the flow cytometric analysis, FITC- or PE-conjugated mouse IgG was used as the negative control. Simultaneously, NK-YS, NK92, and NKL cells were analyzed in a similar manner for the expression of surface markers, and the results were compared.

Unconjugated antibodies against interleukin receptors were as follows:

GM-CSFR (CD116), IL4R (CD124), and IL6R (CD126) from Immunotech (Marseilles, France); and G-CSFR (CD114), IL2Rb (CD122), IL3R (CD123), IL5R (CD125), and IL7 (CD127) from PharMingen (San Diego, Calif.).

After binding these unconjugated antibodies as first antibodies to the cells, the cells were stained with PE-conjugated second antibodies and analyzed with a flow cytometer.

The results of immunophenotyping are summarized in Table 1. The NK-TY2 cells expressed CD2, CD16, CD33, CD38, and CD56 antigens but did not show detectable levels of surface CD3, CD4, CD8, CD19, CD20, and CD34 antigens. The leukemic cells from peripheral blood expressed CD2, CD7, and CD56. Thus, the phenotype of the original leukemic cells was well-preserved in the NK-TY2 cells. The expression of CD33 seemed to be induced during the culture process.

TABLE 1

|       | NK-TY2 | NK-YS | NK92 | NKL |
|-------|--------|-------|------|-----|
| CD1   | −      | −     | −    | −   |
| CD2   | +++    | +++   | +++  | +++ |
| CD3   | −      | −     | −    | −   |
| CD4   | −      | −     | −    | −   |
| CD5   | −      | ++    | −    | −   |
| CD7   | ++     | ++    | ++   | ++  |
| CD8   | −      | −     | −    | −   |
| CD10  | −      | −     | −    | −   |
| CD11a |        |       |      |     |
| CD11b |        |       |      |     |
| CD11c |        |       |      |     |
| CD13  | −      | −     | −    | −   |
| CD15  | −      | −     | −    | −   |
| CD16  | +++    | −     | −    | ++  |
| CD18  |        | ++    |      |     |
| CD19  | −      | −     | −    | −   |
| CD20  | −      | −     | −    | −   |
| CD21  | −      | −     | −    | −   |
| CD22  | −      | −     | −    | −   |
| CD25  | −      | +++   | +++  | +++ |
| CD33  | ++     | −     | −    | −   |
| CD34  | −      | −     | −    | −   |
| CD38  | +++    | +++   | +++  | +++ |
| CD40  | −      | −     | −    | −   |
| CD41  | −      | −     | −    | −   |
| CD43  |        | +++   |      |     |
| CD44  |        | +++   |      |     |
| CD45  | +      | +++   |      |     |
| CD54  |        | +++   |      |     |
| CD56  | +++    | +++   | +++  | +++ |
| CD57  | −      | −     | −    | −   |
| CD58  |        | +++   |      |     |
| CD62L | −      | −     |      |     |

TABLE 1-continued

|       | NK-TY2 | NK-YS | NK92 | NKL |
|-------|--------|-------|------|-----|
| CD70  |        | ++    |      |     |
| CD80  |        | ++    |      |     |
| CD94  | +++    | +     |      |     |
| CD95  | +++    | +++   |      |     |
| CD103 | −      | −     |      |     |
| CD114 |        | −     |      |     |
| CD116 | −      | −     |      |     |
| CD117 | −      | −     |      |     |
| CD123 | −      | −     |      |     |
| CD124 | −      | −     |      |     |
| CD125 | −      | −     |      |     |
| CD126 | −      | −     |      |     |
| CD127 | −      | +     |      |     |

Example 4

Flow Cytometric Analysis <2>(Cancer- or Apoptosis-Associated Gene

Similarly to Example 3, NK-TY2 cells were analyzed by single-color immunofluorescence with a flow cytometer (FACScan; Becton Dickinson and Co., Mountain View, Calif.) for the expression of oncogene or anti-oncogene products. Antibodies used are shown below:

FITC-conjugated anti-bcl2 antibody (Dakopatts);

PE-conjugated anti-p53 antibody (Pharmingen);

anti-bcl6 antibody (Dakopatts);

anti-bclXL antibody (Zymed Laboratories); and anti-c-myc antibody (Oncogene Science)

Simultaneously, NK-YS, TIM96, Daudi, Raji, K562, and U937 cells were analyzed in a similar manner and the results were compared.

Each of the cell lines was stained by a standard direct or indirect conjugating method after permeabilization using Fix and Perm kits (Caltag). Specifically, cells were fixed with reagent A (fixation reagent) at room temperature (RT) and then treated with reagent B (permeabilization reagent) for 15 min. Then, cells were washed and analyzed by a flow cytometer. According to the indirect conjugating method, cells were further reacted with an FITC-conjugated second antibody (Becton Dickinson) for 15 min, washed with PBS, and analyzed with a flow cytometer. Throughout the flow cytometric analyses, an FITC- or PE-conjugated class matched mouse IgG, or a class matched first antibody for indirect method was used as the negative control.

Figure 4:
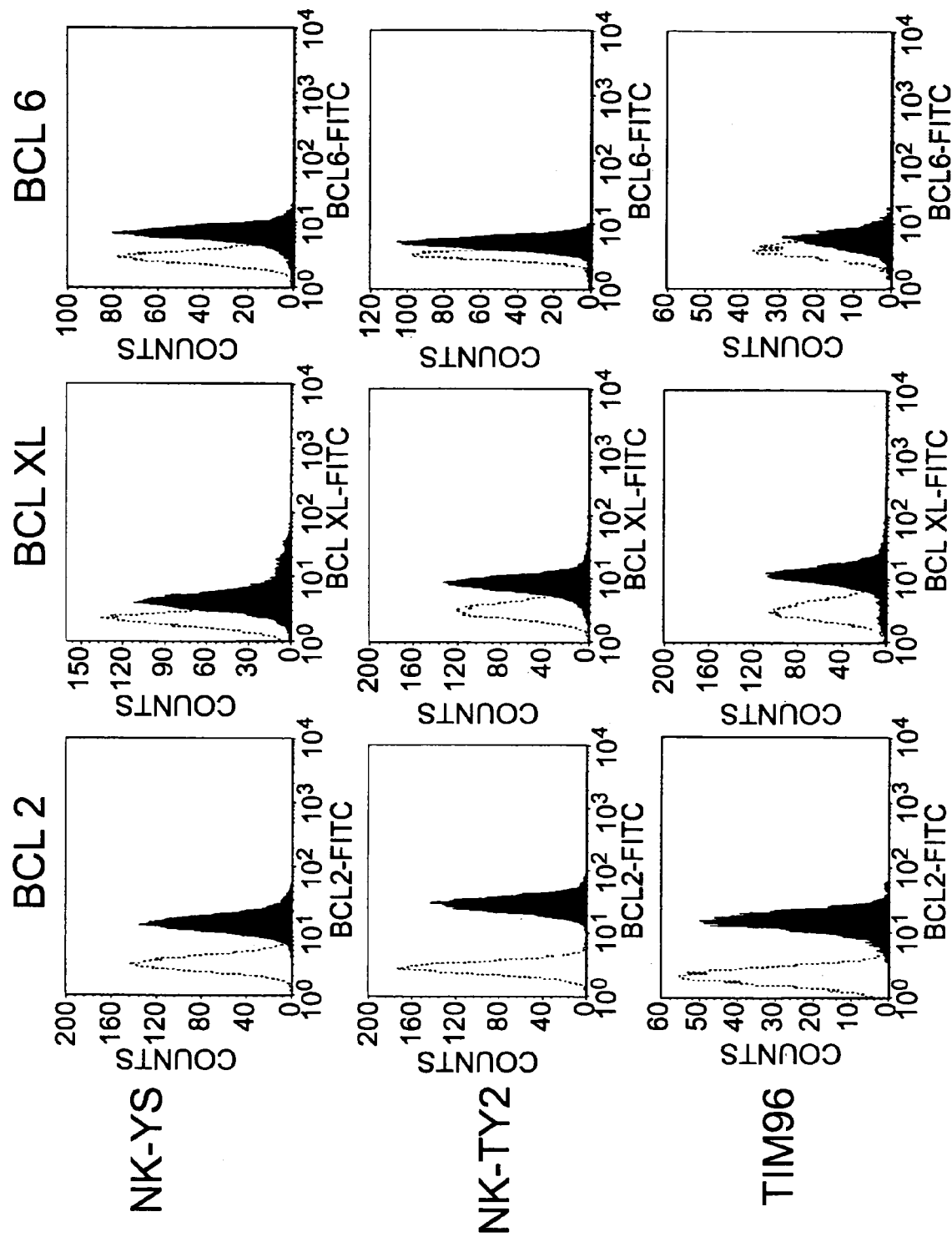
FIG. 4 depicts diagrams showing analysis results of NK-YS, NK-TY2, and TIM96 for BCL2, BCLXL, and BCL6 by flow cytometry.
Figure 5:
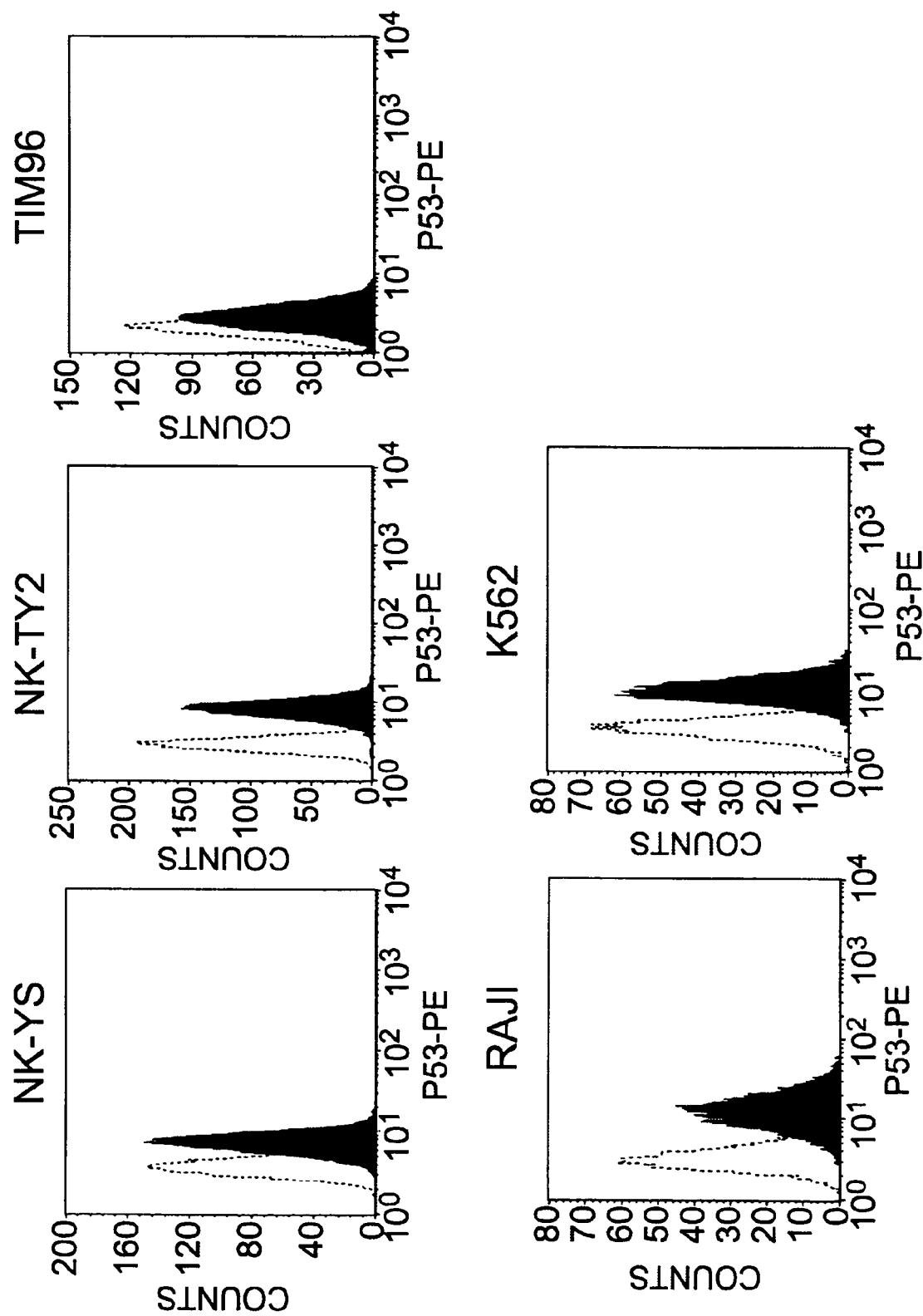
FIG. 5 depicts diagrams showing analysis results of NK-YS, NK-TY2, TIM96, Raji, and K562 for p53 by flow cytometry.
Figure 6:
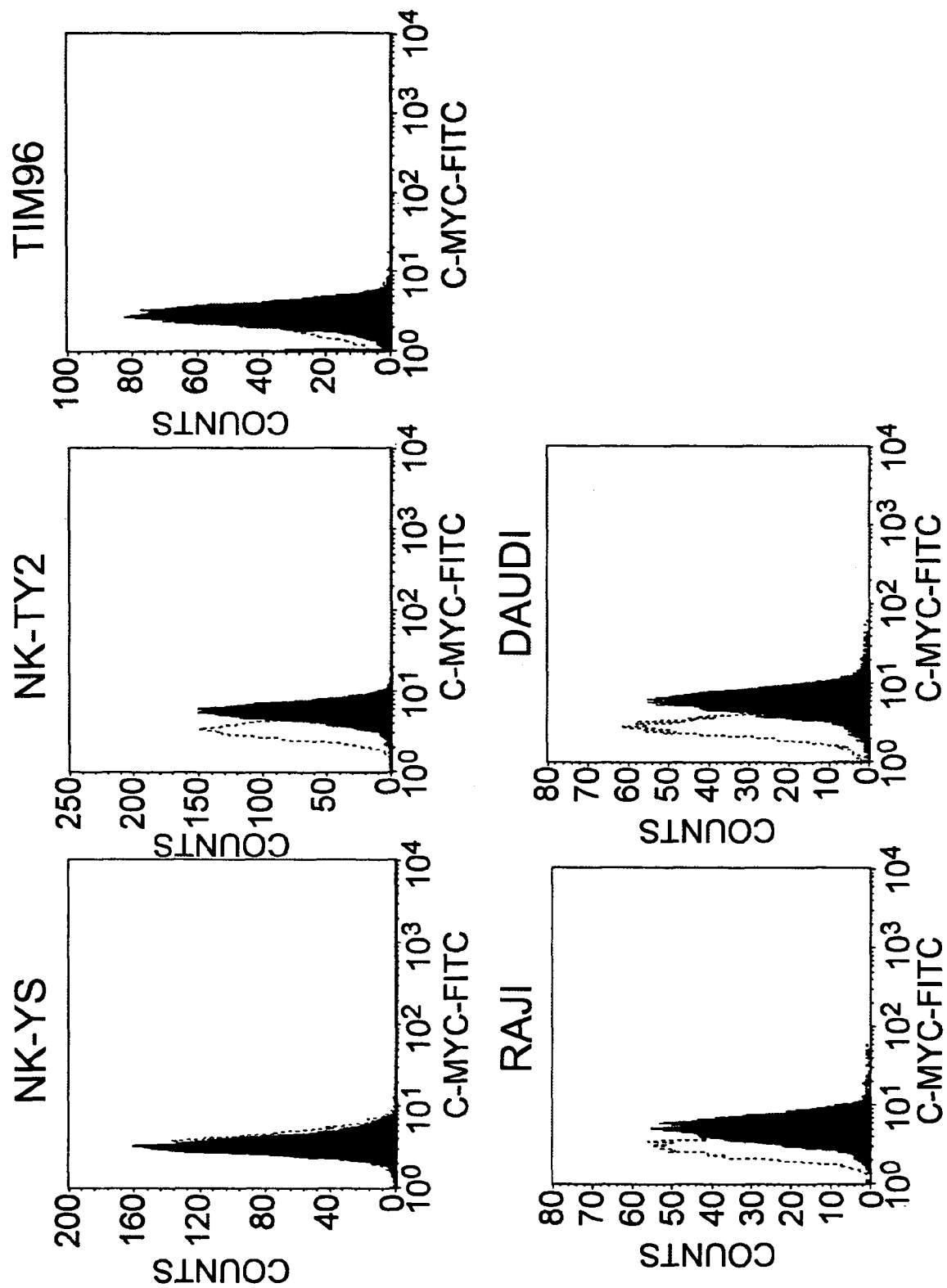
FIG. 6 depicts diagrams showing analysis results of NK-YS, NK-TY2, TIM96, Raji, and Daudi for C-MYC protein by flow cytometry.

The results of the flow cytometric analyses are shown in FIG. 4 (bcl2, bclWL, and bcl6), FIG. 5 (p53), and FIG. 6 (c-myc). Similarly to the NK-YS cell line, NK-TY2 cells expressed bcl2, bclXL, and bcl6 proteins. However, the expression levels of c-myc and p53 protein were higher than in NK-YS cells, and were comparable to Burkitt's lymphoma cell line, Daudi or Raji. These findings showed that EBV genome was easily eliminated during culture due to the activation of the c-myc gene. These results suggest that overexpression of c-myc and p53 substitute the role of EBV genome in the NK-TY2 cell line.

Takata et al. reported the occurrence of EBV-negative clones in a culture of Akata cells derived from EBV-positive Burkitt's lymphoma. Based on the analysis of the EBV-negative clones, they revealed that EBV confers malignant phenotypes of Burkitt's lymphoma, i.e., apoptosis resistance. The same analysis also indicated that EBV is not essential for in vitro growth of Burkitt's lymphoma. Indeed, EBV-negative cases account for 50% of Burkitt's lymphomas in Japanese patients.

In contrast, EBV is detected in all primary nasal angiocentric lymphoma cases. Additionally, there is no report describing the elimination of EBV in EBV-positive NK lymphoma cell lines during culture. Thus, EBV is predicted to play an important role in the growth of EBV-positive NK lymphoma.

Example 5

Expression of NK Receptors

NK receptor expression in NK-TY2, NK-YS, NK92, and NKL cells were analyzed by indirect staining methods. NK-TY2 cells expressed CD94 and NKG2A molecules, but not CD158a, CD158b, CD158c, CD159, and CD161. In contrast, NK-YS cells expressed low levels of CD158b, CD158c, CD94, and NKG2A (Table 2).

TABLE 2

|        | NK-TY2 | NK-YS | NK92 | NKL |
|--------|--------|-------|------|-----|
| CD94   | ++     | +     |      |     |
| CD158a | −      | −     |      |     |
| CD158b | −      | +/−   |      |     |
| CD158c | −      | +     |      |     |
| CD159  | −      | −     |      |     |
| CD161  | −      | −     |      |     |
| NKG2A  | +++    | +     |      |     |

Example 6

Chromosomal Analysis

The cell growth of NK-TY2 cells in the logarithmic phase of cell growth was arrested by a treatment with 0.01 mg of colcemid for 30 min before hypotonic treatment with 0.075 M KCl. The cells were fixed with a 3:1 mixture of methanol and acetic acid. The fixed cell suspension was dropped onto a glass slide and flame-dried. The conventional G-banding method was used for karyotyping. The result is shown in FIG. 7.

Seven of the 11 analyzed fresh leukemic cells in metaphase showed complicated karyotype of 47, X, −X, add(3) (p21), add(4) (q31), +add(6) (q13), +7, add(9) (p13), del(11) (q13q21), der(17)t(1;17)(q12;q25)ins(17;?)(q25;?), −18, +21, der(22)t(18;22) (q11;p13) (data not shown). In the analyzed cells, additional chromosomal abnormalities such as del (X) (p22), −add(4), +add(4)(q31), −6, −add(9), +add(9) (p13), −10, add(14)(q22), −15, +18, +22, −der(22)t(18;22), and +2 mar were observed.

Figure 7:
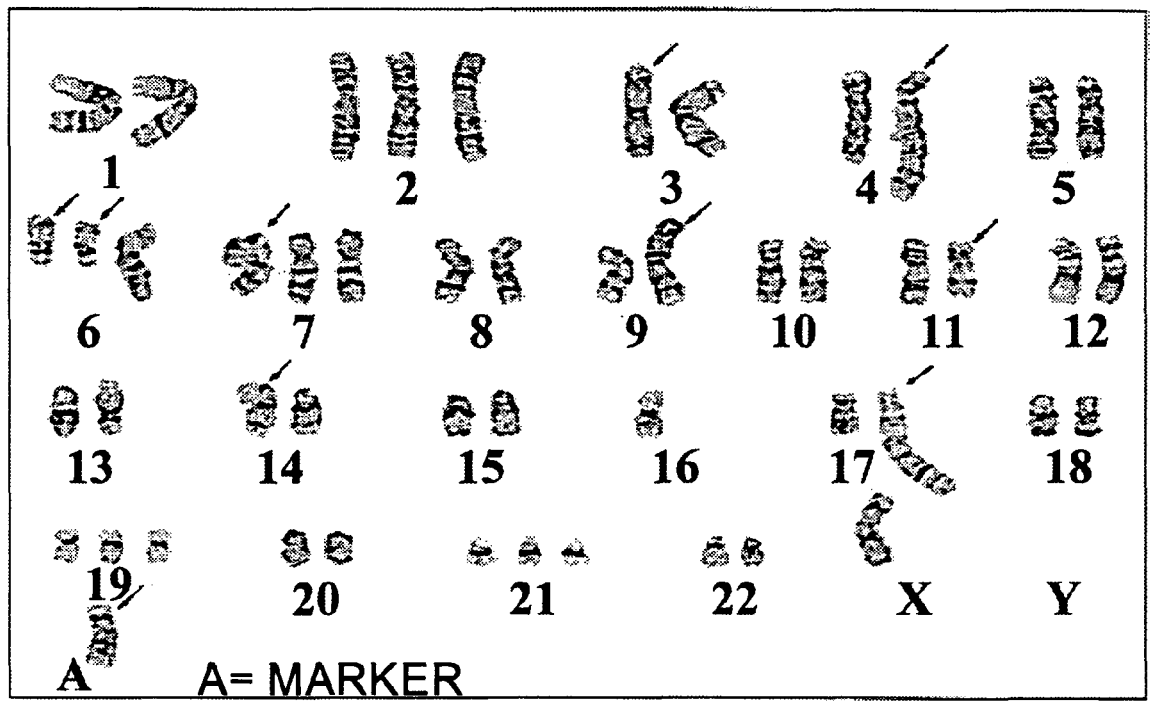
FIG. 7 depicts a photograph showing the result of chromosome analysis of an NK-TY2 cell.

The G-banding analysis showed that 10 of the 10 analyzed NK-TY2 cells in metaphase had a karyotype of 50, X, −X, +2, add(3) (p21), der(4)t(4;9) (q35;q12), del(6) (q13), +del(6), +I(7) (q10), add(9)(p22), del(11) (q13q21), der(14;16) (q10; p10), der(17)dup(17) (q21q25)t(1;17) (q12;q25), +19, +21, +mar (FIG. 7). The NK-TY2 cells preserved the common chromosomal abnormalities of −X, add(3)(p21), del(11)(q13q21), der(17)t(1;17) (q12;q25) observed in the original leukemic cells.

Example 7

Southern Blotting Analysis of T Cell Receptor Genes <1>

The rearrangement of the T cell receptor (hereinafter abbreviated as "TcR") β- and γ-chain genes was evaluated according to a standard method. Specifically, 5 μg DNA cells was extracted from NK-TY2 according to a standard method, digested with EcoRI, HindIII, BamHI, or BglII, electrophoresed on a 0.6% agarose gel, and then transferred onto a nitrocellulose filter. DNA extracted from human placenta was used as the negative control. The filter was hybridized with a $^{32}$P-labelled Cβ2 or Jγ probe and washed under appropriate stringency condition, and then the bands were visualized by autoradiography. LAD, NK-YS, and Jurkat cell lines were similarly analyzed, and the results were compared.

Figure 8:
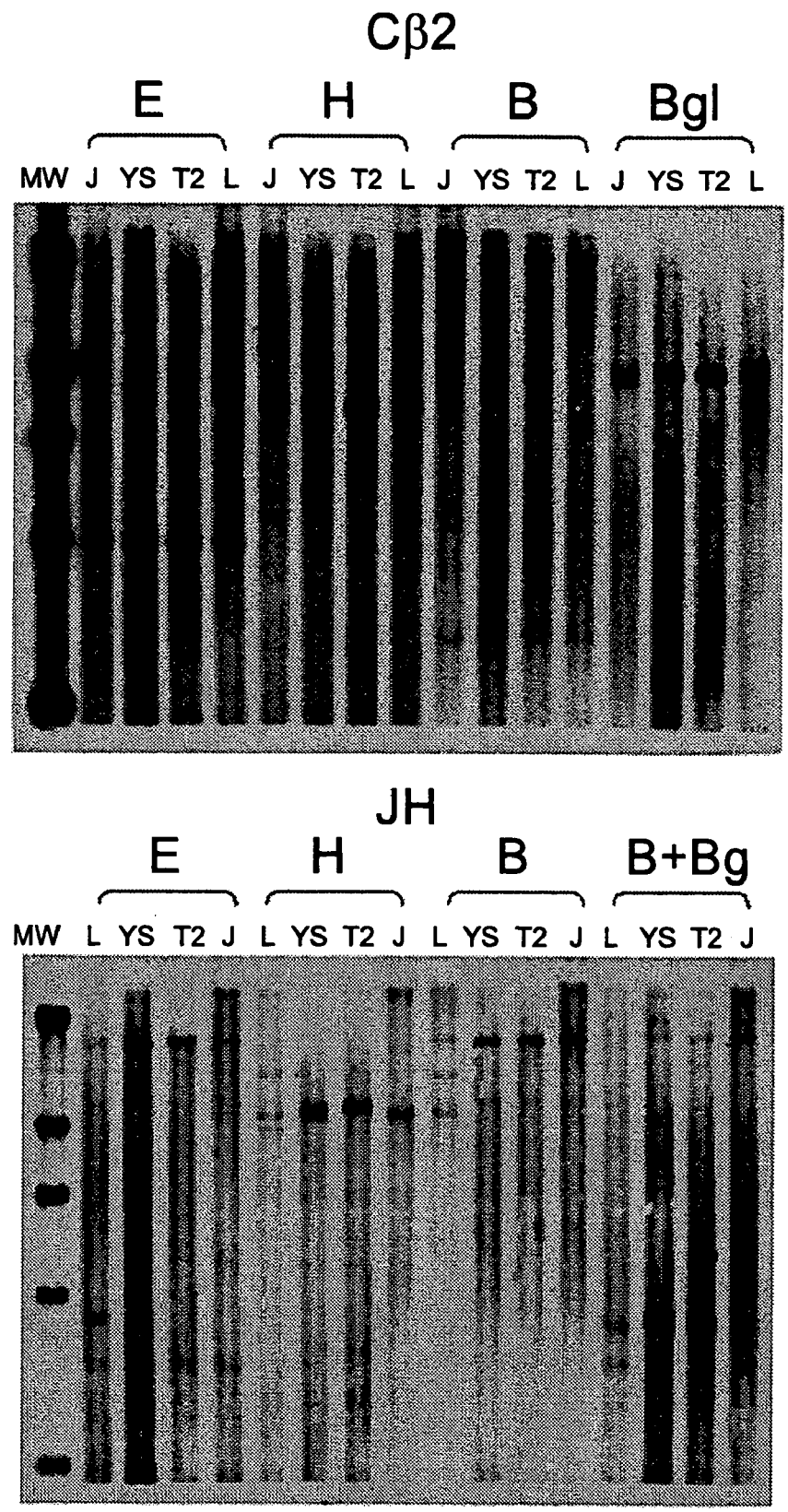
FIG. 8 depicts photographs showing the Southern blot analysis result of the T cell receptor gene. The upper panel shows the result obtained with the Cβ2 probe; the lower panel shows the result obtained with the Jγ probe. In the figure, L indicates LAD cell; YS, NK-YS cell; TY2, NK-TY2 cell; and J, Jurkat cell.

The TcR β- and γ-chain genes of the NK-TY2 cells showed a germline configuration (FIG. 8). This finding agreed with the information obtained from biopsy specimens derived from the skin lesion (data not shown). In addition, the gd_chain also showed a germline configuration. Since the sample of fresh leukemic cells was limited, the rearrangement of the TcR β- and γ-chain genes in these cells was not analyzed.

Example 8

Southern Blotting Analysis of T Cells Receptor Genes <2>

Figure 9:
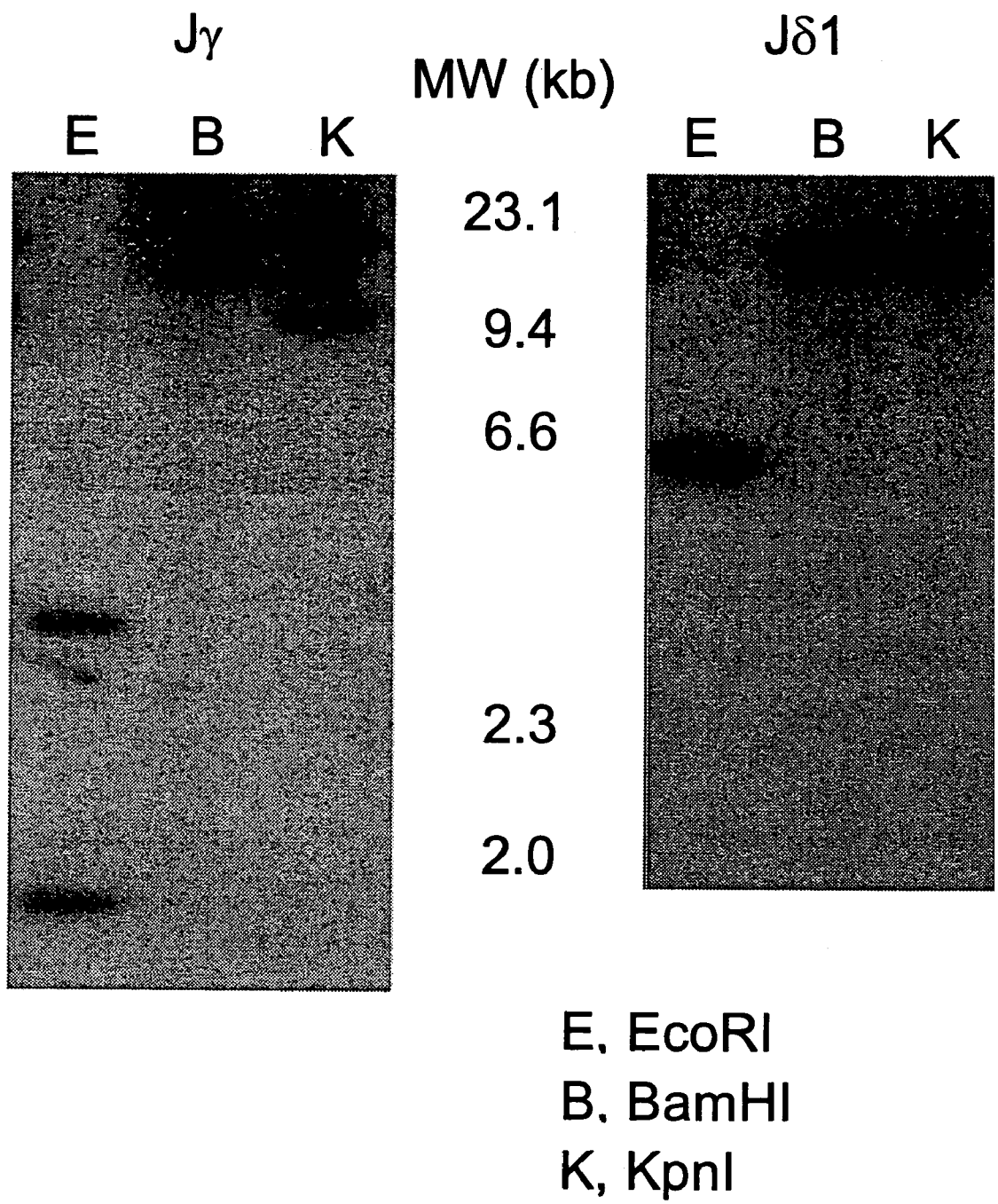
FIG. 9 depicts photographs showing the Southern blot analysis result of NK-TY2 cells for the T cell receptor gene. The right panel shows the result obtained with the Jδ1 probe; the left panel shows the result obtained with the Jγ probe.

The rearrangement of TcRγ- and TcRδ-chain genes in NK-TY2 cells was analyzed similarly as in Example 7. Extracted DNAs were digested with EcoRI, BamHI, or KpnI. Jγ and Jδ1 were used as probes. The result is shown in FIG. 9. No rearranged band could be recognized for TcRγ and TcRδ.

Example 9

Detection of EBV Genome

DNA samples were extracted from NK-TY2 cells, EBV-transformed B lymphoblast-like cell line (LAD) as a positive control, NK-YS cells as a negative control, and Jurkat cells according to a standard method. Resulting DNAs were digested with EcoRI, PstI, BamHI, and BglII restriction enzymes, electrophoresed, and blotted onto nitrocellulose filters. These filters were hybridized with a $^{32}$P-labeled cDNA probe of the EBV terminal repeat, and washed under appropriate stringency condition, and the bands were then visualized by autoradiography.

Figure 10:
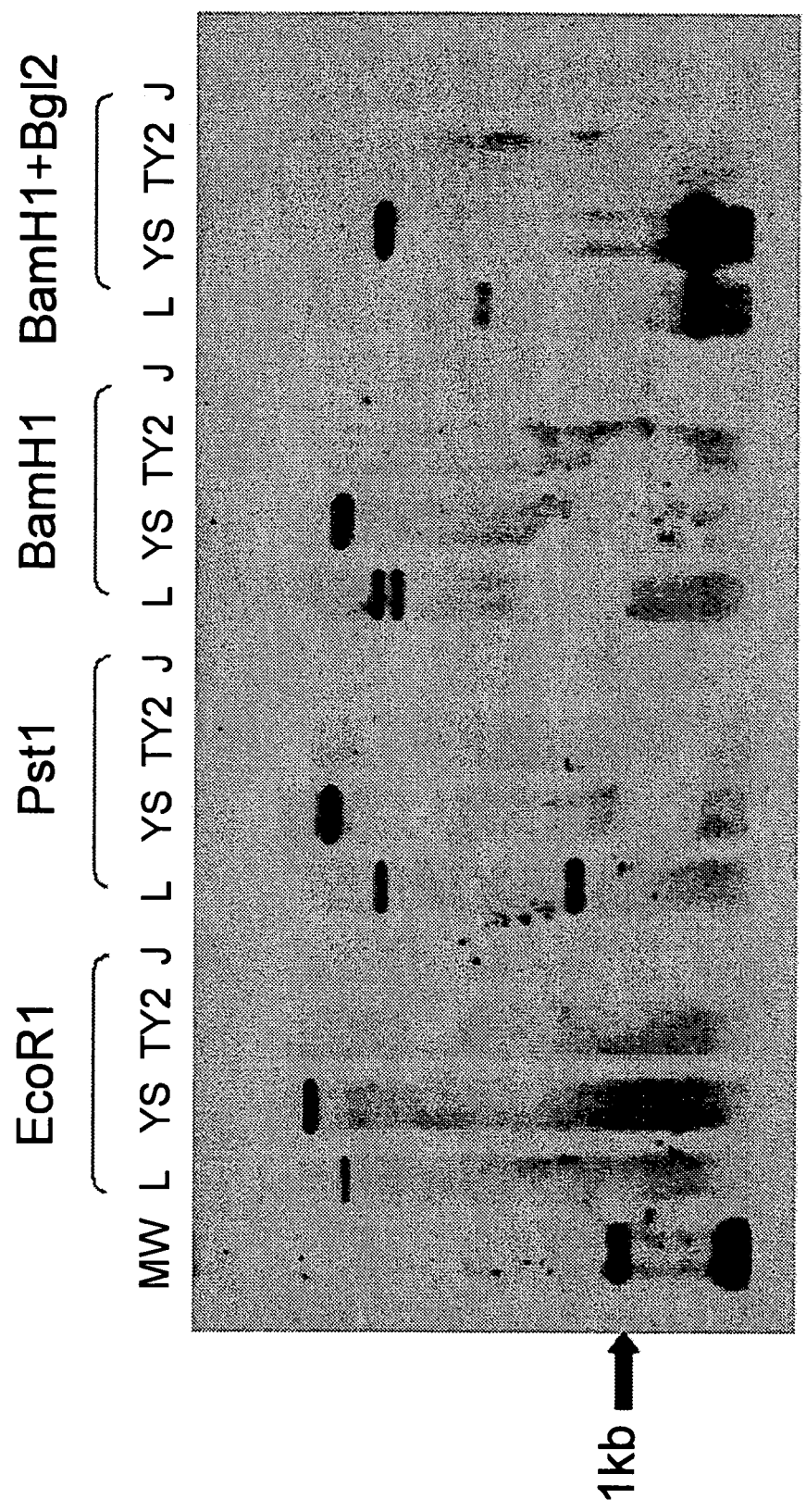
FIG. 10 depicts a photograph showing the Southern blot analysis results of EBV genome. In the figure, L indicates LAD cell; YS, NK-YS cell; TY2, NK-TY2 cell; and J, Jurkat cell.

No EBV terminal repeat was detected for the NK-TY2 cells by the Southern blotting analysis (FIG. 10). In contrast, biopsy specimens were positively stained with EBER-1 antisense oligonucleotide by the in-situ hybridization method. These findings indicate that the NK-TY2 cells lost the EBV genome during the culture process.

INDUSTRIAL APPLICABILITY

The present invention provides EBV-negative NK cell lines. The cell lines of the present invention are EBV-negative, and thus provide experimental conditions devoid of the influence of EBV. Thus, the mechanism underlying the oncogenesis of NK cells due to factors other than EBV can be elucidated using the cell lines of the present invention.

A method of screening for a compound that has the ability to control NK cell activity can be established using the NK cell lines of the present invention. NK cells play an important role in the biological defense mechanism. Thus, a compound that controls NK cell activity can be used to modify functions in the biological defense mechanism. Furthermore, compounds that directly act not on EBV but on NK cells can be screened using the EBV-negative NK cells. Moreover, novel physiologically active substances produced by the NK cells can be screened using the NK cells of the present invention. In addition, the NK cell lines of the present invention find use in experiments for introducing foreign genes using EBV as the vector.

The invention claimed is:

1. An isolated cell of an Epstein-Barr virus (EBV)-negative natural killer (NK) cell line obtained by culturing EBV-positive NK lymphoma cells, wherein the cell overexpresses c-myc.

2. An isolated cell of an EBV-negative NK lymphoma cell line obtained by culturing EBV-positive NK lymphoma cells, wherein the cell overexpresses c-myc and the EBV-positive NK lymphoma cells are nasal angiocentric lymphoma cells.

3. An EBV-negative NK cell line obtained by culturing EBV-positive NK lymphoma cells, wherein the cells of the cell line overexpress c-myc.

4. A cell of the cell line designated NK-TY2 and deposited in the International Patent Organism Depositary of the National Institute of Advanced Industrial Science and Technology of Japan (AIST) under the accession number FERM BP-7865.

5. A cell line designated NK-TY2 and deposited in the International Patent Organism Depositary of the National Institute of Advanced Industrial Science and Technology of Japan (AIST) under the accession number FERM BP-7865.

6. A method of making an EBV-negative NK cell line, the method comprising:
providing a population of peripheral blood cells from a human subject who has lymphoma and who is EBV-positive;
isolating mononuclear cells from the population of peripheral blood cells, the mononuclear cells comprising EBV-positive NK cells;
maintaining the isolated mononuclear cells in culture under conditions and for a time sufficient for loss of EBV from at least some of the NK cells to occur;
selecting one or more NK cells in which the absence of EBV is confirmed; and
culturing the selected NK cell or cells,
thereby providing an EBV-negative NK cell line derived from an EBV-positive NK lymphoma cell, wherein the cells of the cell line overexpress c-myc.

7. The method of claim 6, wherein the lymphoma is a primary nasal lymphoma.

8. The method of claim 6, wherein the mononuclear cells are maintained in culture for at least four months.

9. The method of claim 6, wherein the cells of the EBV-negative NK cell line express CD56.

10. An EBV-negative cell line produced by the method of claim 6.

11. The method of claim 6, further comprising infecting the cells of the cell line with EBV.

12. An EBV-infected cell line produced by the method of claim 11.

13. A method of preparing the cell of claim 2, the method comprising:
  providing a population of peripheral blood cells from a human subject who has nasal angiocentric lymphoma and who is EBV-positive;
  isolating mononuclear cells from the population of peripheral blood cells, the mononuclear cells comprising EBV-positive nasal angiocentric NK lymphoma cells;
  maintaining the isolated mononuclear cells in culture under conditions and for a time sufficient for loss of EBV from at least some of the NK lymphoma cells to occur; and
  selecting an NK lymphoma cell in which the absence of EBV is confirmed;
thereby providing an isolated EBV-negative NK lymphoma cell, wherein the cell overexpresses c-myc.

14. The method of claim 13, wherein the mononuclear cells are maintained in culture for at least four months.

15. The method of claim 13, wherein the EBV-negative NK lymphoma cell expresses CD56.

16. An isolated EBV-negative NK cell produced by the method of claim 13.

17. The method of claim 13, further comprising
  culturing the isolated EBV-negative NK lymphoma cell to produce a population of EBV-negative NK lymphoma cells;
  infecting the population of EBV-negative NK lymphoma cells with EBV to produce a plurality of EBV-infected NK lymphoma cells; and
  isolating an EBV-infected NK lymphoma cell from the plurality,
thereby producing an isolated EBV-infected NK lymphoma cell.

18. An isolated EBV-infected cell produced by the method of claim 17.

19. A method of identifying a modulator of NK cell activity, the method comprising:
  a. providing the cell line of claim 5;
  b. contacting the cell line with a test compound; and
  c. comparing an activity of the cell line in the presence of the test compound to that of a control cell line in the absence of the test compound, wherein the activity is selected from the group consisting of:
    i. cellular proliferation, and
    ii. production of a factor by the cell line;
wherein a test compound that increases or decreases the activity of the cell line as compared to the control is a modulator of NK cell activity.

20. The method of claim 19, further comprising selecting the test compound if it increases or decreases the activity of the cell line.

21. A method of identifying a modulator of NK cell activity, the method comprising:
  a. providing the isolated cell of claim 2;
  b. contacting the isolated cell with a test compound; and
  c. comparing an activity of the isolated cell in the presence of the test compound to that of a control cell in the absence of the test compound, wherein the activity is selected from the group consisting of
    i. cellular proliferation, and
    ii. production of a factor by the isolated cell;
wherein a test compound that increases or decreases the activity of the isolated cell as compared to the control is a modulator of NK cell activity.

22. The method of claim 21, wherein the cell line is the cell line designated NK-TY2 and deposited in the International Patent Organism Depositary of the National Institute of Advanced Industrial Science and Technology of Japan (AIST) under the accession number FERM BP-7865.

23. The method of claim 21, further comprising selecting the test compound if it increases or decreases the activity of the isolated cell.

24. A kit comprising the cell line of claim 3 and a reagent suitable for assaying an activity of the cell line, wherein the activity is selected from the group consisting of (a) cellular proliferation and (b) production of a factor by the cell line.

* * * * *